(12) United States Patent
Fidler et al.

(10) Patent No.: US 6,620,843 B2
(45) Date of Patent: Sep. 16, 2003

(54) ANTICANCER TREATMENT USING TRIPTOLIDE PRODRUGS

(75) Inventors: John M. Fidler, Oakland, CA (US); Ke Li, San Jose, CA (US)

(73) Assignee: Pharmagenesis, Palo Alto, CA (US)

( * ) Notice: Subject to any disclaimer, the term of this patent is extended or adjusted under 35 U.S.C. 154(b) by 101 days.

(21) Appl. No.: 09/766,156

(22) Filed: Jan. 19, 2001

(65) Prior Publication Data

US 2002/0099051 A1 Jul. 25, 2002

(51) Int. Cl.⁷ .............................................. A61K 31/34
(52) U.S. Cl. ..................... 514/473; 514/23; 514/53; 514/54; 514/232.8; 514/254.11; 514/321; 514/338; 514/414; 514/415; 514/422; 514/427; 514/428; 514/461; 514/468; 514/475; 514/908
(58) Field of Search .................... 514/468, 473, 514/908, 23, 53, 54, 232.8, 254.11, 321, 338, 414, 415, 422, 427, 428, 461, 475

(56) References Cited

U.S. PATENT DOCUMENTS

| 4,005,108 A | | 1/1977 | Kupchan et al. |
| 5,663,335 A | * | 9/1997 | Qi et al. ...................... 544/153 |
| 5,919,816 A | * | 7/1999 | Hausheer et al. ........... 514/449 |
| 5,962,516 A | | 10/1999 | Qi et al. |
| 6,150,539 A | | 11/2000 | Musser |

FOREIGN PATENT DOCUMENTS

| WO | WO97/31921 | 9/1997 |

* cited by examiner

Primary Examiner—Frederick Krass
(74) Attorney, Agent, or Firm—LeeAnn Gorthey; Perkins Coie LLP

(57) ABSTRACT

Water soluble triptolide prodrugs are used as anticancer agents, and are found to be more effective in vivo, at lower doses, in reducing tumor size than the widely used chemotherapeutic agents 5-fluorouracil and irinotecan.

18 Claims, 6 Drawing Sheets

US 6,620,843 B2

ANTICANCER TREATMENT USING TRIPTOLIDE PRODRUGS

FIELD OF THE INVENTION

The present invention relates to anticancer treatment using compounds which are water-soluble prodrugs of triptolide or its derivatives.

BACKGROUND OF THE INVENTION

Although many cancers can be cured by surgical resection, chemotherapy is often used as an adjunct to surgical therapy, and is used primarily in the treatment of nonoperable or metastatic malignancy.

Colorectal cancer is a disease that kills nearly half of those afflicted within 5 years of initial diagnosis, and approximately one in 17 Americans develop colorectal cancer during their lifetime. Surgical intervention is not an option for most patients with advanced metastatic colorectal cancer. Initial chemotherapy with fluorouracil (5-FU) and leucovorin has become the standard for patients with stage III colon cancer (NIH Consensus Conference, "Adjuvant therapy for patients with colon and rectal cancer", *JAMA* 264: 1444–1450, 1990; Goldberg R M and Erlichman C, *Oncology* 12: 59–63, 1998). Irinotecan is currently used to treat patients with 5-FU-refractory advanced colorectal cancer (Van Cutsem E and Blijham G H, *Semin Oncol* 26: 13–20, 1999; Cunningham D et al., *Lancet* 352: 1413–1418, 1998).

Breast cancer is the second most common form of cancer among women in the U.S., and the second leading cause of cancer deaths among women. In treatment of breast cancer, adjuvant systemic therapy is begun soon after primary therapy (surgery and radiation therapy) to delay recurrence and/or to prolong survival. Current treatment regimens include a combination regimen of cyclophosphamide, methotrexate and 5-fluorouracil (CMF), as well as the anthracyclines, doxorubicin (adriamycin) and epirubicin, and, for treatment of advanced and metastatic cancers, the taxanes, paclitaxel (Taxol) and docetaxel (Taxotere).

Prostate cancer is the most common cancer in men, with an estimated 244,000 cases in 1995 in the United States. It is the second leading cause among men who die from neoplasia, with an estimated 44,000 deaths per year. Prostate cancer has been found to be relatively resistant to conventional cytotoxic chemotherapy, and toxicity can make such therapy unsuitable for elderly patients. Where prostate cancer is localized, detected early, and the patient's life expectancy is 10 years or more, radical prostatectomy offers the best chance for eradication of the disease; however, patients with bulky, high-grade tumors, or who are older or less healthy, are less likely to be successfully treated by radical prostatectomy. Radiation therapy may be used as an alternative, but long-term recurrence of the disease is a problem.

In view of the high number of deaths each year resulting from cancer, a continuing need exists to identify effective and relatively nontoxic chemotherapeutic drugs for use as anticancer agents.

SUMMARY OF THE INVENTION

In one aspect, the invention provides a method of anticancer treatment. The method comprises administering to a subject in need of such treatment, an effective amount of a triptolide prodrug, as represented by any of structures I–IV, as shown and described below, or a pharmaceutically acceptable salt thereof, in a pharmaceutically acceptable vehicle. Preferred compounds are those of structure I; a particularly preferred compound is triptolide 14-succinate, designated herein as PG490-88. In preferred embodiments, the method is used for treatment of cancer or tumors of the colon, lung, breast, or prostate. The invention also provides pharmaceutical compositions for anticancer or antitumor treatment, consisting essentially of a triptolide prodrug as represented by any one of structures I–IV, as shown and described below, or a pharmaceutically acceptable salt thereof, in a pharmaceutically acceptable vehicle. The compositions are employed in anticancer treatment methods as described herein.

These and other objects and features of the invention will become more fully apparent when the following detailed description of the invention is read in conjunction with the accompanying drawings.

BRIEF DESCRIPTION OF THE DRAWINGS

In FIG. 5, upper bars represent tumor volume at day zero, and lower bars represent tumor volume at day 16 of treatment. Percentages represent percent increase (or decrease) in volume at day 16.

DETAILED DESCRIPTION OF THE INVENTION

I. Definitions

Figure 1A:
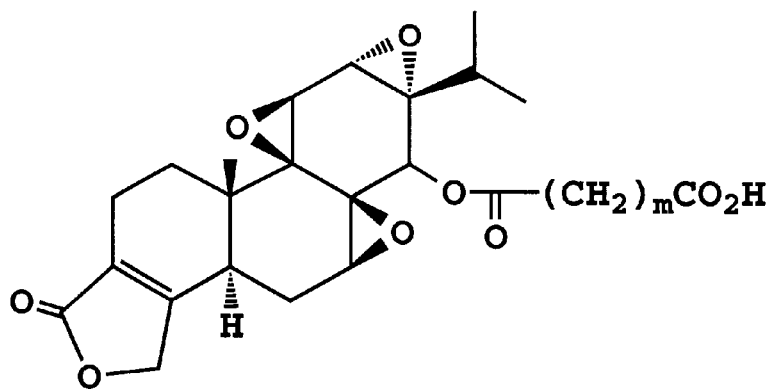
FIGS. 1A–C show examples of specific embodiments of structure I.
Figure 1B:
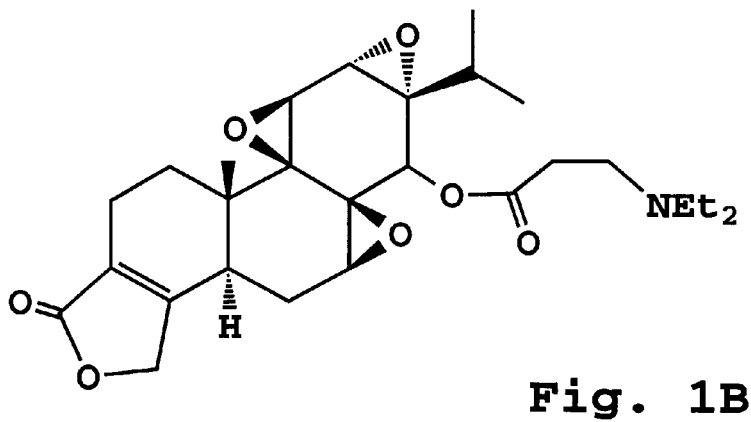
Figure 1C:
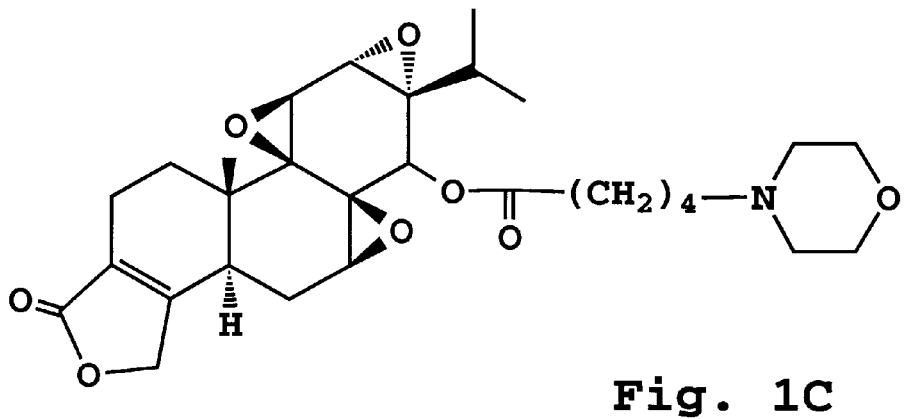
Figure 2A:
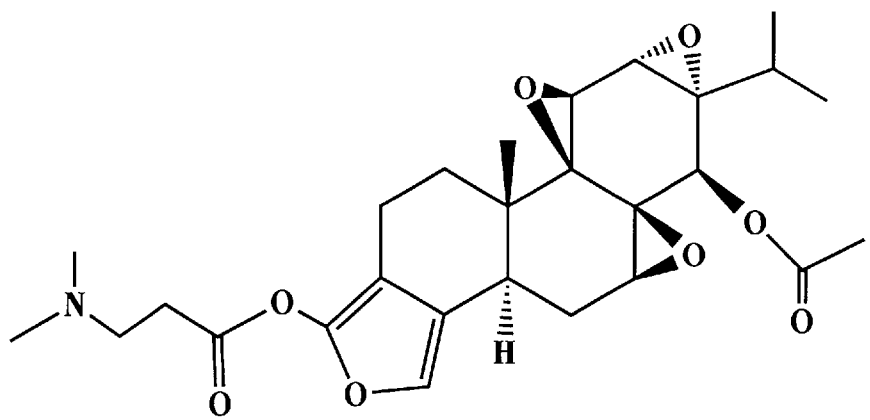
FIGS. 2A–C show examples of specific embodiments of structure II.
Figure 2B:
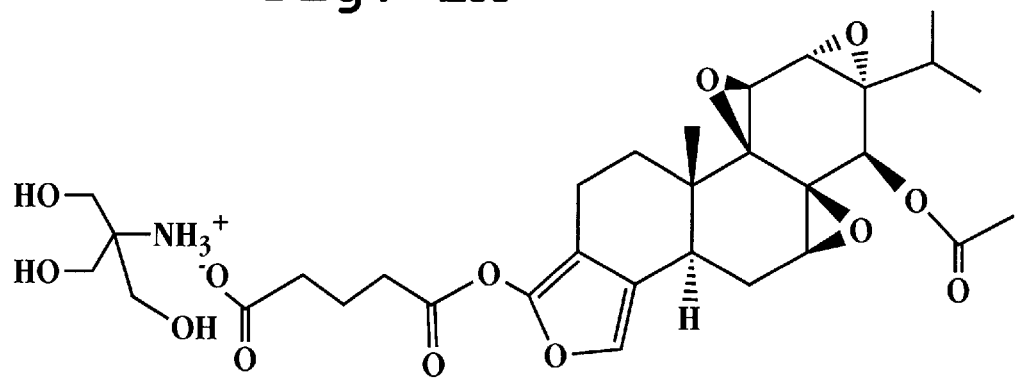
Figure 2C:
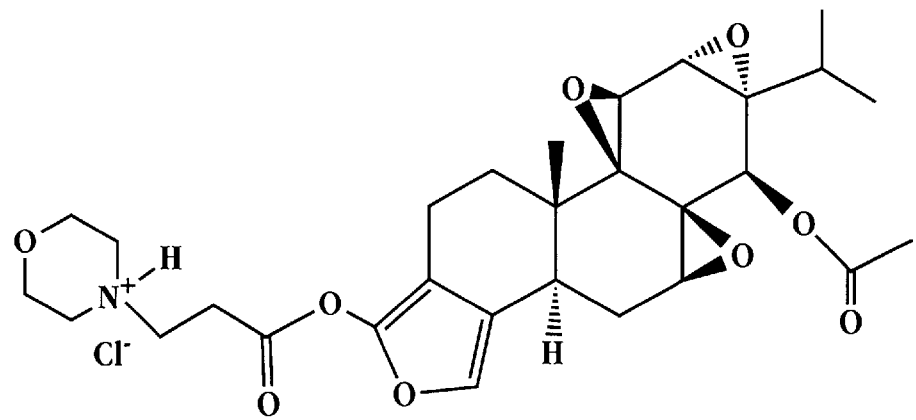
Figure 3A:
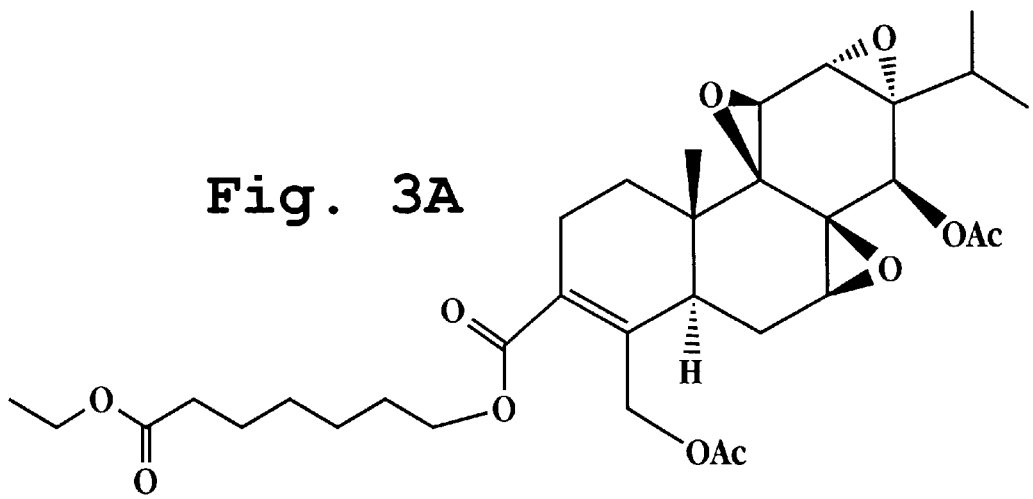
FIGS. 3A–C show examples of specific embodiments of structure III.
Figure 3B:
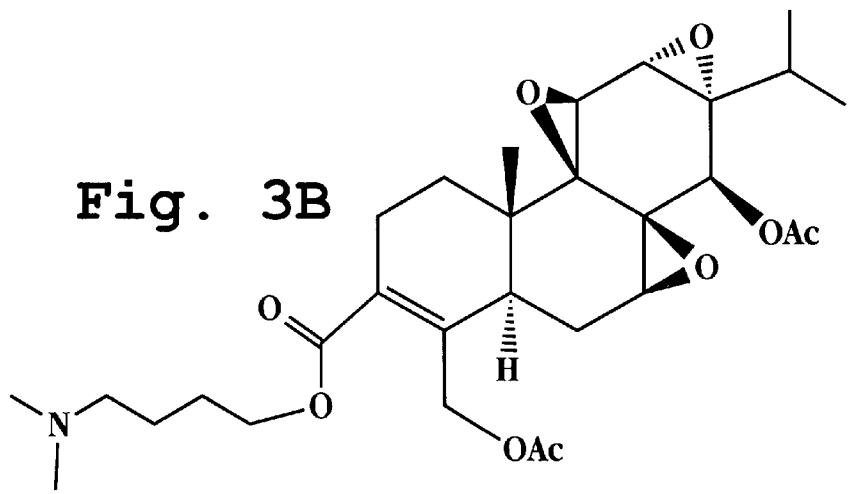
Figure 3C:
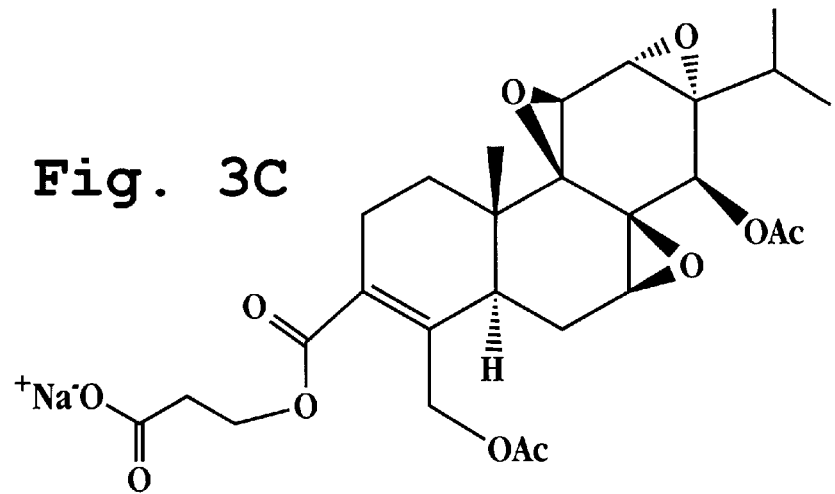
Figure 4A:
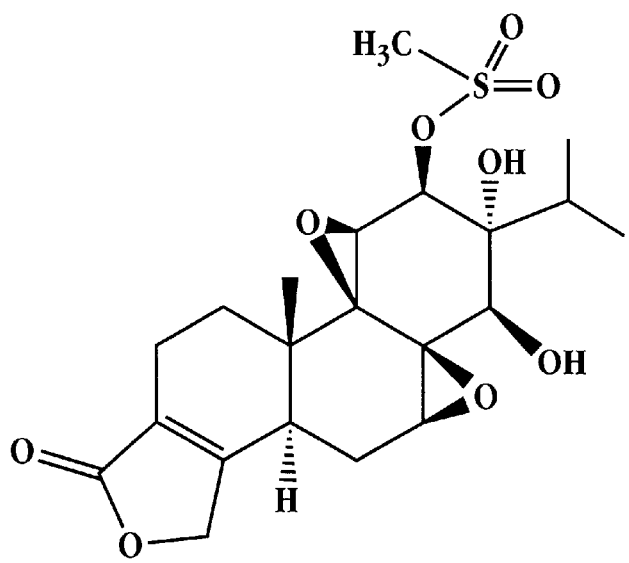
FIGS. 4A–C show examples of specific embodiments of structure IV.
Figure 4B:
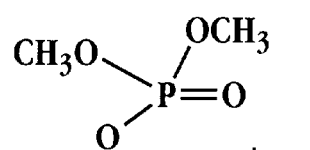
Figure 4B:
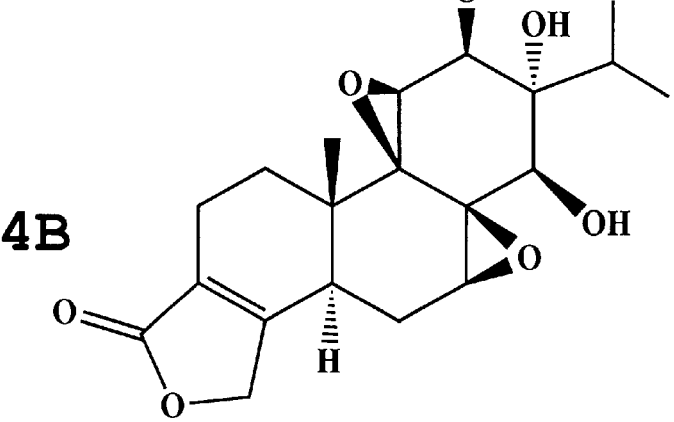
Figure 4C:
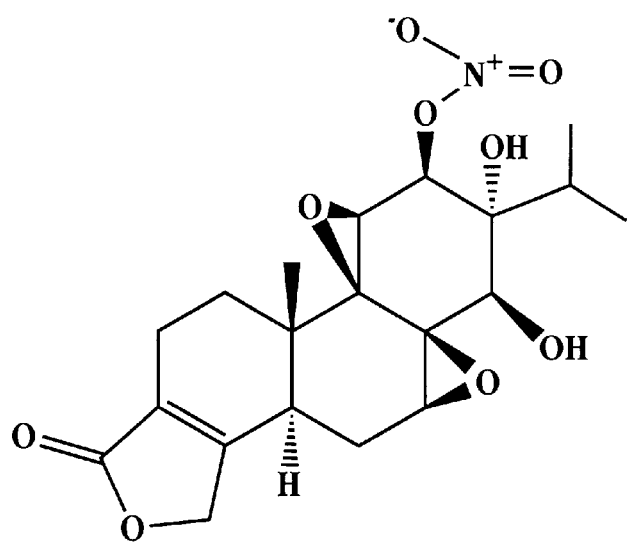

The terms below have the following meanings unless indicated otherwise.

"Alkyl" refers to a fully saturated acyclic monovalent radical containing carbon and hydrogen, which may be branched or a straight chain. Examples are methyl, ethyl, n-butyl, t-butyl, n-heptyl, and isopropyl. "Cycloalkyl" refers to a fully saturated cyclic monovalent radical containing carbon and hydrogen, which may be further substituted with alkyl. Examples are cyclopropyl, methyl cyclopropyl, cyclobutyl, cyclopentyl, and cyclohexyl. "Lower alkyl" refers to an alkyl radical of one to six carbon atoms, preferably one to four carbon atoms, as exemplified by methyl, ethyl, n-butyl, i-butyl, t-butyl, isoamyl, n-pentyl, and isopentyl.

"Alkenyl" refers to a monovalent or divalent unsaturated, preferably mono-unsaturated, radical containing carbon and hydrogen, and which may be cyclic, branched or a straight chain. "Lower alkenyl" refers to such a radical having one to four carbon atoms.

"Acyl" refers to a radical having the form —C(O)R, where R is an alkyl, aryl, or an aralkyl group.

"Aryl" refers to a substituted or unsubstituted monovalent aromatic radical having a single ring (e.g., benzene) or two condensed rings (e.g., naphthyl). This term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl.

"Aralkyl" refers to an alkyl, preferably lower alkyl, substituent which is further substituted with an aryl group; one example is a benzyl group.

A "heterocycle" refers to a non-aromatic ring, preferably a 5- to 7-membered ring, whose ring atoms are selected from the group consisting of carbon, nitrogen, oxygen and sulfur. Preferably, the ring atoms include 3 to 6 carbon atoms. Such heterocycles include, for example, pyrrolidine, piperidine, piperazine, and morpholine.

The term "pharmaceutically acceptable salt" encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethyl ammnonium, bis(2-hydroxyethyl)ammonium, phenylethylbenzylammonium, dibenzylethylenediammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term also includes salts formed by standard acid-base reactions with basic groups, such as amino groups, having a counterion derived from an organic or inorganic acid. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and the like.

A "triptolide derivative" or "triptolide analog," as described herein, refers to a compound based on triptolide, 16-hydroxytriptolide or tripdiolide (2-hydroxytriptolide) which is derivatized at the 12,13-epoxy group or at the lactone ring of the parent compound.

For the purposes of the current disclosure, the following numbering scheme is used for triptolide and triptolide analogs:

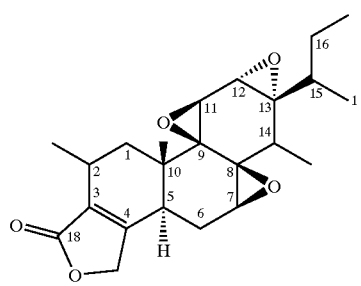

II. Triptolide Prodrugs

Triptolide is obtained from the root xylem of the Chinese medicinal plant *Tnipterygium wilfordli* (TW). The TW plant is found in the Fujiang Province and other southern provinces of China; TW plant material can generally be obtained in China or through commercial sources in the United States. Methods for preparing triptolide and derivatives thereof are known in the art and are described, for example, in Lipsky et al. (U.S. Pat. No. 5,294,443; 1994), Zheng et al. (*Zhongguo Yixue Kexueyuan Xuebao* 13:391, 1991; *Zhongguo Yixue Kexueyuan Xuebao* 16:24, 1994), and Ma et al. (*J. Chin. Pharm. Sci.* 1: 12, 1992). The compounds are widely reported as immunosuppressive compounds and are also reported to have antileukemic activity (Kupchan S M et al., *J. Am. Chem. Soc.* 94:7194, 1972; U.S. Pat. No. 4,005,108 (1977)). However, the administration and therapeutic effectiveness of these compounds have been limited by their low water solubility.

Triptolide prodrugs, as represented by formulas I–IV below, have been described in co-owned U.S. Pat. Nos. 5,663,335, 5,962,516, and 6,150,539, which are hereby incorporated by reference in their entirety. The compounds may be prepared from triptolide, obtained from the root xylem of the Chinese medicinal plant *Tripterygium wilfordii* (TW) or from other known sources, as described in the above-referenced patents. These compounds, which are derivatives of triptolide having hydrophilic substituents, possess greater water solubility than the non-derivatized starting compound, and are effective to hydrolyze and convert in vivo to the parent compound.

Although each of structures I–IV shows a compound modified at one location on the triptolide nucleus, compounds having more than one such modification are also contemplated. The compounds are useful for anticancer therapy, as demonstrated below.

A. Compounds of Structure I

In one aspect, the invention provides an anticancer treatment employing a compound having the structure represented by Formula I below:

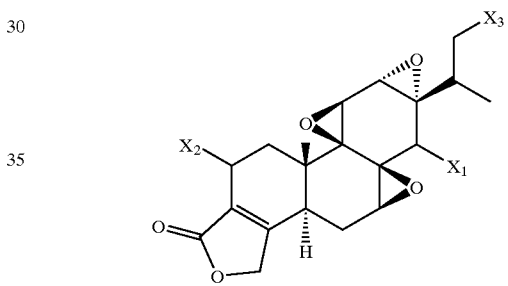

wherein $X^1$ is OH or $OR^1$, and $X^2$ and $X^3$ are independently OH, $OR^1$ or H, with the proviso that at least one of $X^1$, $X^2$ and $X^3$ is $OR^1$, and at least one of $X^2$ and $X^3$ is H; and $R^1$ is —C(O)—Y—Z, wherein Y is a branched or unbranched $C_1$–$C_6$ alkyl or alkenyl chain; and Z is $COOR^2$, $NR^3R^{3'}$, or $^+NR^4R^{4'}R^{4''}$, where $R^2$ is hydrogen or a cation; $R^3$ and $R^{3'}$ are independently H or branched or unbranched $C_1$–$C_6$ alkyl, hydroxyalkyl, or alkoxyalkyl, or $R^3$ and $R^{3'}$ taken together form a 5- to 7-member heterocyclic ring whose ring atoms are selected from the group consisting of carbon, nitrogen, oxygen and sulfur, wherein the ring atoms include 2 to 6 carbon atoms, one or more nitrogen atoms, and optionally one or more oxygen or sulfur atoms, and wherein the ring is unsubstituted or is substituted with one or more groups selected from $R^5$, $OR^5$, $NR^5R^6$, $SR^5$, $NO_2$, CN, $C(O)R^5$, $C(O)NR^5R^6$, $OC(O)R^5$, $OC(O)NR^5R^6$, and halogen (fluoro, chloro, bromo, or iodo), where $R^5$ and $R^6$ are independently hydrogen, lower alkyl or lower alkenyl; and $R^4$, $R^{4'}$, and $R^{4''}$ are independently branched or unbranched $C_1$–$C_6$ alkyl, hydroxyalkyl or alkoxyalkyl.

In one general embodiment, the compound is a derivative of triptolide, wherein $X_1$ is OH or $OR_1$ as defined above, and $X^2$ and $X^3$ are H. This includes the compound designated herein as PG490-88, where Y is $C_2$ (i.e. —$CH_2CH_2$—), and Z is *COOH or $COOR^2$, where $R^2$ is a cation. In a second general embodiment, the compound is a derivative of 16-hydroxyl triptolide, wherein $X_1$ and $X_3$ are OH or $OR_1$, and $X_2$ is H. In a third general embodiment, the compound is a derivative of tripdiolide (2-hydroxytriptolide), wherein $X_1$ and $X_2$ are OH or $OR_1$, and $X^3$ is H.

In one preferred embodiment, Z is COOH or $COOR^2$, where $R^2$ is a metal ion, preferably $Na^+$ or $K^+$. In an alternative embodiment, $R^2$ is an organic ammonium ion, protonated if necessary, preferably selected from lysine, triethylamine, or tris(hydroxymethyl)aminomethane. Preferably, $R^2$ is $Na^+$, tris(hydroxymethyl)aminomethane or lysine, and Y is a $C_1$–$C_4$ alkyl chain.

In another preferred embodiment, Z is $NR^3R^{3'}$, where $R^3$ and $R^{3'}$ are independently H or branched or unbranched $C_1$–$C_6$ alkyl, or together form a 5- to 7-member heterocyclic ring containing 2 to 6 carbon atoms, one or more nitrogen atoms, and optionally one or more oxygen or sulfur atoms. Preferably, Z is dimethylamino, diethylamino, or N-morpholino, and Y is a $C_1$–$C_4$ alkyl chain.

Where Z is a quaternary or protonated tertiary amino group, the compound also includes an anionic counterion. The anionic counterion is preferably a halide or a carboxylate-, sulfonate-, or sulfate-containing ion. More preferably, the counterion is chloride, bromide, acetate, oxalate, maleate, fumarate, methanesulfonate, or toluenesulfonate.

Preparation of these compounds is described in co-owned U.S. Pat. No. 5,663,335. Preparation of compounds of structures II–IV, below, is described in co-owned U.S. Pat. No. 6,150,539.

B. Compounds of Structure II

In the compounds of structure II, below:

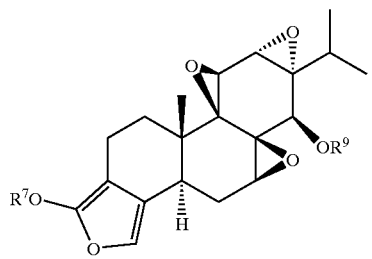

$OR^7$ is a hydrolyzable, hydrophilic group, e.g. a carboxylic ester, an inorganic ester, or a mono-, di- or trisaccharide linked to the parent compound via an anomeric oxygen. The carboxylic or inorganic ester has a central atom selected from carbon, sulfur, phosphorus, and boron, and attached to the central atom, at least one oxygen atom, and at least one group of the form —O—Y—Z'. In this group, Y represents a branched or unbranched $C_1$–$C_6$ alkyl or alkenyl chain, and Z' represents hydrogen, or, preferably, a polar group selected from keto, aldehyde, carboxylate, carboxylic ester, hydroxy, alkoxy, polyether, thiol, alkylthio, amino, alkylamino, cyano, nitro, sulfate, nitrate, phosphate, or a 5- to 7-membered heterocyclic ring whose ring atoms are selected from the group consisting of carbon, nitrogen, oxygen and sulfur, where the ring atoms include 3 to 6 carbon atoms. Such heterocycles include, for example, pyridine, pyrrolidine, piperazine, and morpholine.

Examples of such inorganic esters include sulfites (—O—S(=O)—OR), sulfinates (—O—S(=O)—R), sulfates (—O—S(=O)$_2$—OR), sulfonates (—O—S(=O)$_2$—R), phosphates (—O—P(=O)(OR)$_2$), phosphonates (—O—P(=O)R(OR)), and borates (—O—B(OR)$_2$).

Where Z' is an anionic species such as a carboxylate, the positively charged counterion is preferably an inorganic metal, such as $Na^+$, $K^+$, or $Mg^{+2}$, or a protonated organic amine, e.g. tromethamine (tris(hydroxymethyl) aminomethane). Where Z is a basic amine, the compound may take the form of a protonated salt, with a negatively charged counterion such as chloride, bromide, iodide, acetate, oxalate, maleate, fumarate, mesylate or tosylate.

The substituent $OR^9$ is OH or O—(C=O)R, where R is lower alkyl.

Preferably, $R^7$ is selected from:

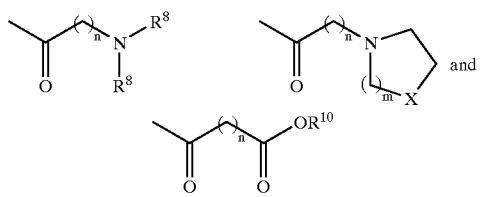

where $R^8$ is lower alkyl, $R^{10}$ is H or lower alkyl, n=0–4, m=1–2, and X=$CH_2$, O, or $NR^8$.

The hydrophilic nature of the substituents increases the aqueous solubility of the compounds, and hydrolysis of $OR^1$ (e.g. in vivo) regenerates the unsaturated lactone (butenolide) of triptolide.

C. Compounds of Structure III

In another embodiment, the triptolide analogs are of the structure III, as shown below:

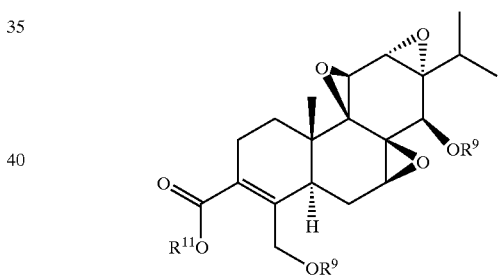

The group $OR^9$ is as defined above, and is preferably lower acyl, e.g. acetyl. The group $OR^{11}$ is preferably of the form —O—Y—Z' or —O—(C=O)—Y—Z', where Y is a branched or unbranched $C_1$–$C_6$ alkyl or alkenyl chain, and Z' is hydrogen or a polar group selected from keto, aldehyde, carboxylate, carboxylic ester, amino, alkylamino, hydroxy, alkoxy, polyether, thiol, alkylthio, cyano, nitro, inorganic ester, or a 5- to 7-member heterocyclic ring whose ring atoms are selected from the group consisting of carbon, nitrogen, oxygen and sulfur, where the ring atoms include 3 to 6 carbon atoms. $R^{11}$ may also be a mono-, di- or trisaccharide linked to C14 at an anomeric center.

Again, where Z' is an anionic species such as a carboxylate, the positively charged counterion is preferably an inorganic metal, such as $Na^+$, $K^+$, or $Mg^{+2}$, or a protonated organic amine, e.g. tromethamine. Where Z' is a basic amine, the compound may take the form of a protonated salt, with a negatively charged counterion such as chloride, bromide, iodide, acetate, oxalate, maleate, fumarate, mesylate or tosylate.

Preferably, $R^{11}$ is of the form:

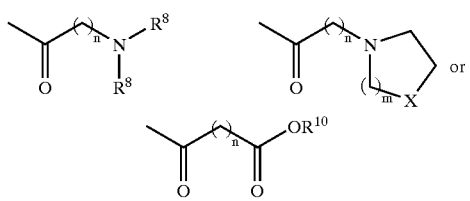

where $R^8$ is lower alkyl, $R^{10}$ is H or lower alkyl, m=1–2, n=1–4, and $X=CH_2$, O, or $NR^8$.

D. Compounds of Structure IV

In a further embodiment, the triptolide analogs have the structure IV, as shown below:

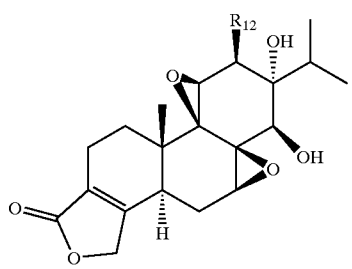

where $-R^{12}$ is a leaving group selected from the group consisting of alkyl sulfonate, fluoroalkyl sulfonate, aryl sulfonate, fluorosulfonate, nitrate, alkyl phosphate, alkyl borate, trialkylammonium, and dialkylsulfonium. Preferred leaving groups are tosylate, mesylate, fluorosulfonate, trifluoromethylsulfonate, nitrate, and alkyl phosphates or boronates, represented by $-OP(O)(OR^{10})_2$, and $-OB(OR^{10})_2$, where $R^{10}$ is hydrogen or lower alkyl. The group $OR^9$ is $-OH$ or $-O-(C=O)-R$, where R is lower alkyl.

III. Therapeutic Compositions

Formulations containing the triptolide analogs described above may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide analog in a suitable intravenous solution, such as sterile physiological salt solution.

Liquid compositions can be prepared by dissolving or dispersing the triptolide analog (about 0.5% to about 20%) and optional pharmaceutical adjuvants in a carrier, such as, for example, aqueous saline, aqueous dextrose, glycerol, or ethanol, to form a solution or suspension. The high water solubility of the compounds of the invention make them particularly advantageous for administering in aqueous solution, e.g. by intraperitoneal injection. Although aqueous solutions are preferred, compositions in accordance with the invention may also be formulated as a suspension in a lipid (e.g., a triglyceride, a phospholipid, or a polyethoxylated castor oil such as "CREMOPHOR EL"™), in a liposomal suspension, or in an aqueous emulsion.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see Remington's Pharmaceutical Sciences (19th Ed., Williams & Wilkins, 1995). The composition to be administered will contain a quantity of the selected compound in a pharmaceutically effective amount for effecting immunosuppression in a subject.

For systemic administration, the composition may be administered orally, transdermally or parenterally, e.g., by intravenous, subcutaneous, intraperitoneal, or intramuscular injection, or by inhalation. Multiple intravenous, subcutaneous and/or intramuscular doses are possible, and in the case of implantable methods for treatment, formulations designed for sustained release are particularly useful. Patients may also be treated using implantable subcutaneous portals, reservoirs, or pumps.

Regional treatment is useful for treatment of cancers in specific organs. Treatment can be accomplished by intraarterial infusion. A catheter can be surgically or angiographically implanted to direct treatment to the affected organ. A subcutaneous portal, connected to the catheter, can be used for chronic treatment, or an implantable, refillable pump may also be employed.

IV. Anticancer Treatment

The triptolide prodrugs may be used for treatment of various cancer cell types, including, but not limited to, breast, colon, small cell lung, large cell lung, prostate, malignant melanoma, liver, kidney, pancreatic, esophogeal, stomach, ovarian, cervical or lymphoma tumors. Treatment of breast, colon, lung, and prostate tumors is particularly contemplated. Treatment of leukemias is also contemplated.

Figure 5:
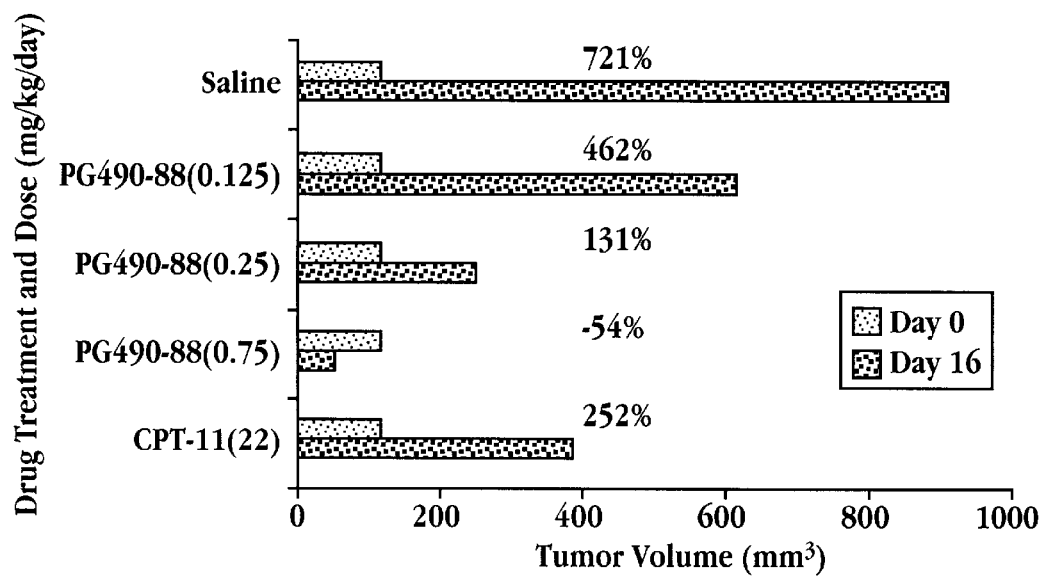
FIGS. 5 and 6 show effectiveness of a triptolide prodrug, triptolide 14-succinate, shown in FIG. 1A where m=2, and designated herein as PG490-88, in treatment of HT-29 human colon tumors in a mouse xenotransplant model.
Figure 6:
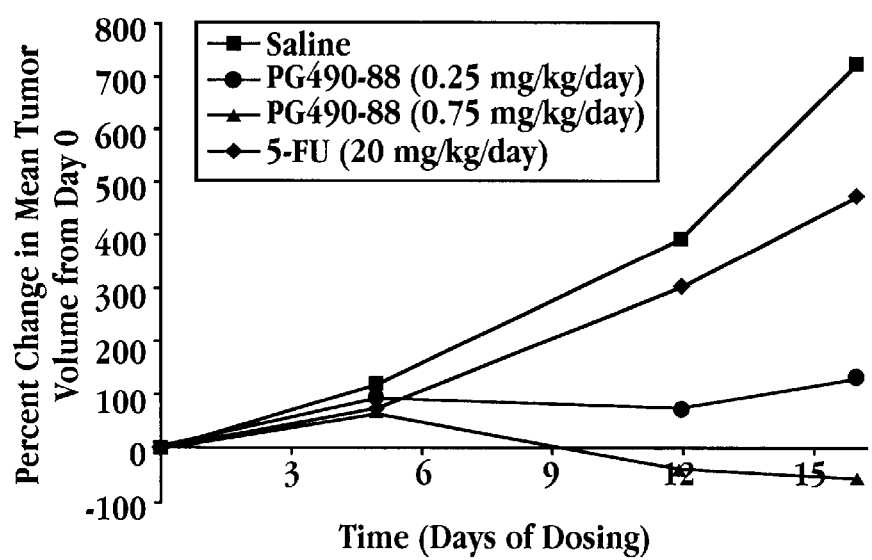

The data presented in FIGS. 5–6 show the effectiveness of a triptolide prodrug, triptolide 14-succinate, designated herein as PG490-88, in treatment of HT-29 human colon tumors in a mouse xenotransplant model, in comparison with two currently preferred treatments for colon cancer. The studies were carried out as described in Materials and Methods, below.

As shown in FIG. 5, PG490-88 inhibited HT-29 tumor growth in a dose-dependent manner, at much lower doses than were required for CPT-11 (irinotecan). By day 16 (lower bars), tumor growth in the mice treated with PG490-

88 at 0.125 mg/kg was slightly inhibited, and the mean tumor volume had increased by 462%, compared to 721% in the vehicle control group. PG490-88 at 0.25 mg/kg produced moderate inhibition, and the mean tumor volume increased by 131%. PG490-88 at 0.75 mg/kg strongly inhibited tumor growth and induced tumor regression. By day 16, the mean tumor volume had decreased 54% from the initial value.

Meanwhile, the tumor growth inhibition by CPT-11 at 22 mg/kg was only slight to moderate, as the mean tumor volume increased by 252% from the initial value. Thus, PG490-88 showed unexpected efficacy in comparison to CPT-11.

5-FU (5-fluorouracil) has been a standard conventional chemotherapy used clinically to treat colon cancer. Compared to 5-FU, PG490-88 also showed unexpectedly superior efficacy with HT-29 tumors (FIG. 6). At 20 mg/kg, 5-FU only slightly inhibited tumor growth, and tumors grew steadily. By day 16, the mean tumor volume of the 5-FU group had grown 470%, compared to 721% in the control group. This dosage is relatively high for 5-FU in this model system; a higher dose of 5-FU (30 mg/kg) showed signs of toxicity.

In comparison, tumor growth in the mice treated with PG490-88 at 0.25 mg/kg was inhibited, and the suppressive effect was particularly evident after day 5. By day 16, the mean tumor volume had increased by only 131% in this treatment group. PG490-88 at 0.75 mg/kg strongly inhibited tumor growth and progressively reduced tumor size from day 5 (FIG. 6). By day 9, the mean tumor volume had decreased from the day 5 value to approximately the initial value. By day 16, the mean tumor volume had decreased by 54% from its original volume.

The triptolide prodrug thus showed unexpected efficacy, at low doses, in comparison to 5-FU and CPT-11 in these studies with tumor xenografts of the HT-29 human colon cancer cell line.

Materials and Methods

Human Tumor Xenograft Study. An HT-29 human colon cancer cell line was purchased from ATCC (Manassas, Va.). Cells were cultured in DMEM (Dulbecco's Modified Eagle's Medium) from GIBIOBRL (Grand Island, N.Y.) with 10% fetal bovine serum (FBS) supplemented with L-glutamine and Penicillin/Streptomycin. The tumor cells were harvested when cultures reached 80–90% confluence. The supernatants were discarded and the cell pellets were suspended to $1 \times 10^8$ cells/ml in DMEM medium without FBS. HT-29 cells ($5 \times 10^6$) were implanted intradermally on the back of each mouse. Tumor size was monitored by measuring the length (L), width (W), and height (H) of each tumor and calculating tumor volume (Vol=½×4/3π×(L/2)× (W/2)×H).

When the tumors reached an appropriate size, the mice were grouped together (5 mice/group) to constitute a similar mean tumor size in the groups within each experiment (approximately 100 mm$^3$), and treatment was initiated at day 0.

Mice bearing human tumor cell xenografts were treated with PG490-88 IP daily for 5 days per week. The compound was administered as the sodium salt. CPT-11 was administered IV twice per week. 5-FU was given IP daily for 5 days per week. The stock solutions of each therapeutic agent were diluted in 0.9% NaCl for dosing. The agents were given to mice at 100 μl per 10 g of mouse body weight. Mice were dosed for two weeks, and 0.9% NaCl was used as the vehicle control. Tumor volume was monitored, and toxicity of the chemotherapeutic treatment was monitored by weighing the mice every day. Results are described above and illustrated in FIGS. 5–6.

While the invention has been described with reference to specific methods and embodiments, it will be appreciated that various modifications may be made without departing from the invention.

It is claimed:

1. A method for inhibiting the growth of a solid tumor, comprising administering to a subject in need of such treatment, in a pharmaceutically acceptable vehicle, an effective amount of a triptolide prodrug, or a pharmaceutically acceptable salt thereof, having a structure selected from:

I:

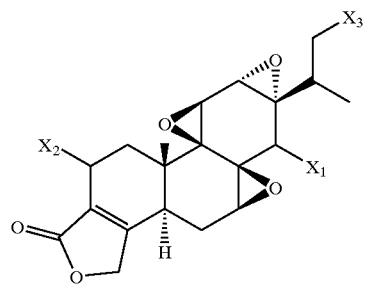

where
$X^1$ is OH or $OR^1$, and $X^2$ and $X^3$ are independently OH, $OR^1$ or H, with the proviso that at least one of $X^1$, $X^2$ and $X^3$ is $OR^1$, and at least one of $X^2$ and $X^3$ is H; and
$R^1$ is —C(O)—Y—Z, wherein
Y is a branched or unbranched $C_1$–$C_6$ alkyl or alkenyl chain; and
Z is $COOR^2$, $NR^3R^{3'}$, or $^+NR^4R^{4'}R^{4''}$, where
$R^2$ is H or a cation;
$R^3$ and $R^{3'}$ are independently H or branched or unbranched $C_1$–$C_6$ alkyl, hydroxyalkyl, or alkoxyalkyl, or $R^3$ and $R^{3'}$ taken together form a 5- to 7-member heterocyclic ring whose ring atoms are selected from the group consisting of carbon, nitrogen, oxygen and sulfur, wherein said ring atoms include 2 to 6 carbon atoms, one or more nitrogen atoms, and optionally one or more oxygen or sulfur atoms, and said ring is unsubstituted or is substituted with one or more groups selected from $R^5$, $OR^5$, $NR^5R^6$, $SR^5$, $NO_2$, $CN$, $C(O)R^5$, $C(O)NR^5R^6$, $OC(O)R^5$, $OC(O)NR^5R^6$, and halogen, where $R^5$ and $R^6$ are independently hydrogen, lower alkyl or lower alkenyl; and
$R^4$, $R^{4'}$, and $R^{4''}$ are independently branched or unbranched $C_1$–$C_6$ alkyl, hydroxyalkyl, or alkoxyalkyl;

II:

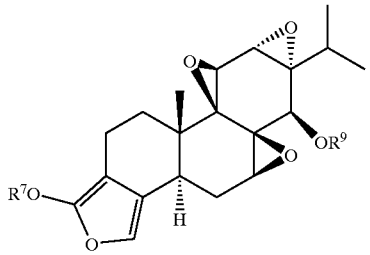

where $OR^7$ is selected from
(i) a carboxylic ester, carbonate, or inorganic ester, having a central atom selected from carbon, sulfur, phosphorus, nitrogen, and boron, and having linked to said central atom at least one group of the form —Y—Z' or —O—Y—Z', where Y is a branched or unbranched C1–C6 alkyl or alkenyl chain, and Z' is hydrogen or a polar group selected from keto, aldehyde, carboxylate, carboxylic ester, hydroxy, alkoxy, polyether, thiol, alkylthio, amino, cyano, nitro, sulfate, nitrate, phosphate, or a 5- to 7-membered heterocycle having ring atoms selected from carbon, nitrogen, oxygen, and sulfur, and three to six carbon ring atoms, and (ii) a mono-, di- or trisaccharide linked to C14 at an anomeric center;

and $OR^9$ is OH or O—(C═O)R, where R is lower alkyl;

III:

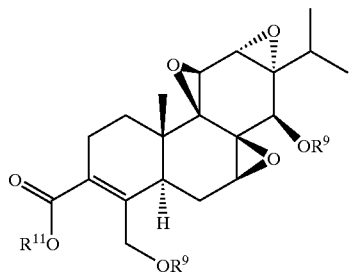

where $OR^{11}$ is selected from (i) —O—Y—Z or —O—(C═O)—Y—Z, where Y is a branched or unbranched C1–C6 alkyl or alkenyl chain, and Z is hydrogen or a polar group selected from keto, aldehyde, carboxylate, carboxylic ester, amino, alkylamino, hydroxy, alkoxy, polyether, thiol, alkylthio, cyano, nitro, inorganic ester, or a 5- to 7-member heterocyclic ring whose ring atoms are selected from the group consisting of carbon, nitrogen, oxygen and sulfur, where the ring atoms include 3 to 6 carbon atoms, and (ii) a mono-, di- or trisaccharide linked to C14 at an anomeric center;

and $OR^9$ is —O—(C═O)R, where R is lower alkyl; and

IV:

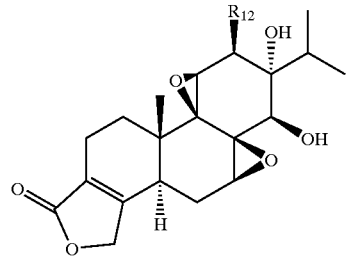

where
$R^{12}$ is a leaving group selected from the group consisting of alkyl sulfonate, fluoroalkyl sulfonate, aryl sulfonate, fluorosulfonate, nitrate, alkyl phosphate, alkyl borate, trialkylammonium, and dialkylsulfonium;

and $OR^9$ is OH or O—(C═O)—R, where R is lower alkyl.

2. The method of claim 1, wherein the triptolide prodrug is of structure I.

3. The method of claim 2, wherein $X^2=X^3=H$.

4. The method of claim 2, wherein Y is —CH$_2$CH$_2$—.

5. The method of claim 4, wherein Z is COOH.

6. The method of claim 4, wherein Z is $COOR^2$, and $R^2$ is a metal ion or an organic ammonium ion.

7. The method of claim 1, wherein the triptolide prodrug is of structure II.

8. The method of claim 7, wherein $R^7$ is selected from group (i).

9. The method of claim 8, wherein $R^7$ is selected from:

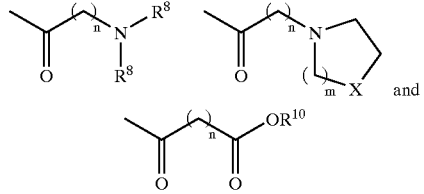

where $R^8$ is lower alkyl, $R^{10}$ is H or lower alkyl, n=1–4, m=1–2, and X═CH$_2$, O, or $NR^8$.

10. The method of claim 1, wherein the triptolide prodrug is of structure III.

11. The method of claim 10, wherein $R^{11}$ is selected from group (i).

12. The method of claim 11, wherein $R^{11}$ is selected from:

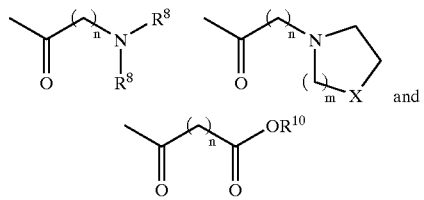

where $R^8$ is lower alkyl, $R^{10}$ is H or lower alkyl, n=1–4, m=1–2, and X═CH$_2$, O, or $NR^8$.

13. The method of claim 1, wherein the triptolide prodrug is of structure IV.

14. The method of claim 13, wherein $R^{12}$ is selected from nitrate, tosylate, mesylate, fluorosulfonate, trifluoromethylsulfonate, —OP(O)(OR$^{10}$)$_2$, and —OB(OR$^{10}$)$_2$, where $R^{10}$ is hydrogen or lower alkyl.

15. The method of claim 1, wherein said solid tumor is a tumor of the colon, breast, lung, or prostate.

16. The method of claim 15, wherein said solid tumor is a tumor of the colon.

17. The method of claim 15, wherein said solid tumor is a tumor of the lung.

18. The method of claim 15, wherein said solid tumor is a tumor of the prostate.

* * * * *